US012616493B2

(12) United States Patent
Hernadi et al.

(10) Patent No.: US 12,616,493 B2
(45) Date of Patent: May 5, 2026

(54) JAW ACTUATION MECHANISM

(71) Applicant: Precision Robotics Limited, London (GB)

(72) Inventors: Tamas Csaba Hernadi, London (GB); Jianzhong Shang, Dartford (GB)

(73) Assignee: Precision Robotics Limited, London (GB)

( * ) Notice: Subject to any disclaimer, the term of this patent is extended or adjusted under 35 U.S.C. 154(b) by 294 days.

(21) Appl. No.: 18/278,077

(22) PCT Filed: Feb. 7, 2022

(86) PCT No.: PCT/GB2022/050316
§ 371 (c)(1),
(2) Date: Aug. 21, 2023

(87) PCT Pub. No.: WO2022/175641
PCT Pub. Date: Aug. 25, 2022

(65) Prior Publication Data
US 2024/0130751 A1    Apr. 25, 2024
US 2024/0225678 A9    Jul. 11, 2024

(30) Foreign Application Priority Data

Feb. 19, 2021    (GB) ..................................... 2102387

(51) Int. Cl.
*A61B 17/29* (2006.01)
*A61B 34/00* (2016.01)
*A61B 34/30* (2016.01)

(52) U.S. Cl.
CPC .............. *A61B 17/29* (2013.01); *A61B 34/30* (2016.02); *A61B 34/71* (2016.02);
(Continued)

(58) Field of Classification Search
CPC ......... A61B 17/29; A61B 34/30; A61B 34/71; A61B 2017/2936; A61B 2017/294; A61B 2034/301
See application file for complete search history.

(56) References Cited

U.S. PATENT DOCUMENTS

2014/0025070 A1* 1/2014 Kerr ....................... A61B 17/29
                                                606/41
2019/0059922 A1   2/2019 Yamanaka
                  (Continued)

FOREIGN PATENT DOCUMENTS

DE    112016006761 T5    1/2019
WO      2015088647 A1    6/2015

OTHER PUBLICATIONS

International Search Report from PCT International Application No. PCT/GB2022/050316 dated Apr. 20, 2022.

*Primary Examiner* — Brooke Labranche
(74) *Attorney, Agent, or Firm* — Budzyn IP Law, LLC

(57) ABSTRACT

An actuation mechanism including: first and second jaws rotatable about a jaw axis, having first and second slots, respectively; and a slider moveable along a slider axis. The slider includes first and second protrusions slidably receivable within the first and second slots, respectively, wherein each slot extends in a direction which is non-parallel to the slider axis when the respective protrusion is engaged with the slot. A return is attachable to the actuation mechanism and an actuation member is operably engageable with both the slider and the return. The actuation member includes first and second ends, a first portion that extends from the first end to the return, and a second portion that extends from the return to the second end. The first portion is fixable to the slider whereby individual movement of the first and second portions relative to the return causes the slider to move.

9 Claims, 3 Drawing Sheets

(52) U.S. Cl.

CPC . *A61B 2017/2936* (2013.01); *A61B 2017/294* (2013.01); *A61B 2034/301* (2016.02)

(56) References Cited

U.S. PATENT DOCUMENTS

| | | |
|---|---|---|
| 2019/0077026 A1 | 3/2019 | Jogasaki et al. |
| 2019/0090894 A1 | 3/2019 | Yamanaka |

* cited by examiner

JAW ACTUATION MECHANISM

CROSS-REFERENCE TO RELATED APPLICATIONS

This Application is a National Stage Application under 35 U.S.C. § 371 of PCT Application No. PCT/GB2022/050316, filed Feb. 7, 2022 which claims priority to UK Patent Application No. GB2102387.4, filed Feb. 19, 2021, the entire contents of which are incorporated by reference herein.

BACKGROUND OF THE INVENTION

1. Field of the Invention

This invention relates to an actuation mechanism, and specifically, but not exclusively to an actuation mechanism which facilitates the actuation of two jaw members with a single pair of tendons. The invention has particular application in the field of surgical robotics to facilitate the actuation of two jaw members forming part of a surgical instrument end effector for minimally invasive surgical procedures, although the invention is not limited to such application and may also have use in other medical/surgical devices or other robotic devices comprising a tendon driven end effector with two or more movable parts, such as jaw members.

Herein the invention is primarily described in relation to application in the field of surgical robotics. However, this is for demonstrative purposes only and is not to the exclusion of the invention's application in other fields.

2. Description of the Related Art

Known surgical instruments forming part of robotic surgical systems comprise a shaft, an articulation portion and an end effector. The shaft may extend from other components of the surgical robot which control and drive movement of the articulation portion and the end effector. The shaft may thereby facilitate positioning of the articulation portion and end effector at the required area of a patient. The articulation portion may comprise a plurality of joints positioned adjacent to one another to provide degrees of freedom of movement to the end effector relative to the shaft. Lastly, the end effector may be adapted to carry out particular actions required in surgical procedures.

Known end effectors include end effectors with two movable jaw members such as graspers, forceps, scissors and dissectors, for example. Some known end effectors are tendon driven meaning that each possible articulation of the end effector is caused by the pulling of a tendon which is anchored to the, or part of the, end effector. Further, known end effectors are driven by antagonistic pairs of tendons to ensure that each articulation may be reversed. For example, if the actuation of a jaw member in a first direction is caused by the pulling of a first tendon then actuation of the jaw member in a second, opposite direction may require the pulling of a second (antagonistic) tendon.

SUMMARY OF THE INVENTION

According to a first aspect of the invention there is provided an actuation mechanism comprising: a first jaw rotatable about a jaw axis and comprising a first slot; a second jaw rotatable about the jaw axis and comprising a second slot; a slider moveable along a slider axis between a first position and a second position and movably engageable with the first and second jaws, which slider comprises a first protrusion slidably receivable within the first slot and a second protrusion slidably receivable within the second slot, wherein each slot extends in a direction which is non-parallel to the slider axis when the respective protrusion is engaged with the slot; a return attachable to the actuation mechanism and spaced apart from the slider; and an actuation member operably engageable with both the slider and the return, the actuation member comprising a first end, a second end, a first portion that extends from the first end to the return, and a second portion that extends from the return to the second end, the first portion being fixable to the slider whereby movement of the first portion away from the return causes the slider to move towards the first position and movement of the second portion away from the return causes the slider to move towards the second position.

In use, when the slider moves along the slider axis between the first and second positions, each of the first and second protrusions may slide within their respective slot. As each slot extends in a direction non-parallel to the slider axis, movement of each protrusion within its respective slot causes the slot to move relative to the slider axis. Movement of each slot is facilitated by rotation of the respective jaw about the jaw axis, therefore movement of the slider causes the jaws to rotate about the jaw axis. Further, each jaw and particularly each slot may be configured so that the jaws rotate about the jaw axis in an opposite sense to one another, i.e. a movement of the slider will cause the first jaw to rotate in a first sense and the second jaw to rotate in a second sense opposite to the first.

The first portion of the actuation member extends from the first end of the actuation member to the return and may be fixed to the slider so that, in use, movement of the first portion away from return causes the slider to move away from the return to a first position. In other words, pulling the first end of the actuation member away from the return causes the slider to move towards the first position. The second portion of the actuation member extends from the return to the second end of the actuation member and is not fixed to the slider. In use, movement of the second portion away from the return causes the first portion of the actuation member to move towards the return and hence causes the slider to move towards a second position. Therefore, pulling the second end of the actuation member away from the return caues the slider to move towards the second position.

Hence, by means of the invention both the first jaw and the second jaw of the actuation mechanism may be rotated in opposite senses to one another simultaneously by actuating a single actuating member. Further, each jaw may be rotated in a first sense or a second sense opposite to the first by actuating the actuation member antagonistically. In other words, moving the first portion of the actuation member away from the return may rotate the jaws towards one another while moving the second portion of the actuation member away from the return may rotate the jaws away from one another.

If the actuation mechanism is used to actuate an end effector of a robotic surgical instrument, for example, the actuation member may extend through an articulation portion of the surgical instrument. The actuation member may be narrow and flexible and, more particularly may be a tendon, rope, wire, thread, string or any other type of member suitable for facilitating a similar means of actuation.

In some known end effectors, each jaw is driven by a separate pair of antagonistic tendons. This means that four tendons are required for operation of the end effector rather than single tendon with first and second portions. Each tendon will have associated moving parts that drive actuation of the tendon and translate the movement of the tendons to the respective jaw of the end effector. Such known end effectors may suffer limitations such as how small the surgical instrument can be to facilitate all four tendons and associated moving parts and how cost effectively it may be manufactured while comprising all of the necessary motors and other components to drive those four tendons. The invention overcomes these disadvantages as only a single tendon is required with first and second portions that each extend through the surgical instrument. Accordingly the surgical instrument may be more compact as fewer tendons need to be accommodated. Also, the number of associated moving parts may be halved, if not reduced further, as a result of there being one tendon only.

The amount of force that may be applied by the jaws and the degree of rotation that is possible are each dependent on the angle of the slots relative to the slider axis. As the slider moves along the slider axis each protrusion transfers a force to the respective jaw via the respective slot. Some of that force is expended causing the jaw to rotate about the jaw axis, some is expended overcoming friction between the protrusion and the slot and it may be considered that the rest is transferred to the jaw and may be applied by the jaw as it opens and closes. A shallower angle between each slot and the slider axis when the slider is in a given position results in the jaw rotating less per unit of movement of the slider along the slider axis and hence less force being expended causing the jaw to rotate. A shallower angle also reduces the force required to overcome friction between the protrusion and the slot. Therefore, a shallower angle results in a greater magnitude of force being transferred to the jaws which may then be applied by the jaws as they open or close.

Convesely, a larger angle between each slot and the slider axis results in the jaws rotating further per unit of movement of the slider along the slider axis at the expense of the magnitude of force which may be applied by the jaws.

The angle of the slots relative to the slider axis and the shape of the slots may be adapted to suit the application so that when the slider is at a given position along the slider axis, the force which may be applied by the jaws is appropriate. Further, the angle and shape of the slots may be adapted so that the jaws can apply different magnitudes of forces when positioned at different angles of rotation relative to the jaw axis. This may allow the forces to be optimised for a particular application.

Each of the slots may extend linearly or non-linearly. Linear slots may provide a simpler relationship between the jaw position and the forces that may be applied and hence allow for more intuitive use of the actuation mechanism. Non-linear slots may allow a greater variety of possible relationships between the jaw position and the forces that may be applied. The relationship may be more complex, which may allow greater optimisation of the actuation mechanism for the application in which it is to be used.

In embodiments of the invention the return may comprise a pulley rotatable about a return axis and the actuation member may pass around the pulley between the first portion and the second portion.

In such embodiments of the invention the pulley may reduce friction resulting from engagement of the actuation member with the return when the actuation member is actuated antagonistically, by moving either the first end or the second end away from the return. Reduced friction may provide advantages such as greater actuation member durability, a lower energy requirement to actuate the actuation member and/or improved performance of the actuation member as the slider, and hence the jaws, may be actuated more accurately and with less likelihood of backlash or jerky movements.

In embodiments of the invention the return may further comprise an axle that extends along the return axis and supports the pulley.

In such embodiments of the invention the pulley may be rotatable about the axle, the axle may be rotatable about the return axis, or both.

In other embodiments of the invention, the return may be fixed relative to the return axis and the return and/or the actuation member may be adapted so that the actuation member may slide over the return with a low coefficient of friction.

In embodiments of the invention the return axis may be coaxial with the jaw axis. Further, in some embodiments of the invention the first and second jaws may be rotatably engageable with the axle such that the first and second jaws are supported by, and rotatable about, the axle.

In such embodiments of the invention, the longitudinal space occupied by the jaws, return and slider may be reduced by virtue of the jaws and the pulley being rotatable about the same axis and the same axle. The actuation mechanism may therefore be more compact overall. The complexity of the actuation mechanism may also be reduced in terms of the number of parts required which may in turn reduce manufacturing cost and improve the durability of the actuation mechanism due to there being fewer parts which may fail.

In embodiments of the invention the actuation member may be slidably engageable with the slider between the return and the second end.

In such embodiments of the invention, the second portion of the actuation member remains moveable relative to the slider to ensure that the slider may move both towards and away from the return. In addition, slidable engagement of the second portion of the actuating member with the slider may improve the stability of the slider as it moves along the slider axis in response to movement of the first portion of the actuation member. In particular, it may reduce the likelihood of the slider twisting due to forces exerted on the first and second protrusions by the respective jaws.

In embodiments of the invention the slider may comprise a first member receiving portion and a second member portion, and the actuation member may be fixable to the slider via the first member receiving portion and slidably receivable within the second member receiving portion.

In such embodiments of the invention the first and second member receiving portions may be formed separate to, and be attachable to, the rest of the slider or the first and second member receiving portions may be integral with the rest of the slider. For example, the first and second member receiving portions may be first and second ferrules that are attachable to the slider by any suitable means, such as by laser spot welding for example. Alternatively the first and second member receiving portions may be first and second channels that extend through the slider.

The first portion of the actuation member may be fixed to the first member receiving portion by any suitable means. For example, if the first member receiving portion is a ferrule, the ferrule may be crimped, glued, laser spot welded or soldered to the actuation member.

In embodiments of the invention each jaw may comprise a tool portion, movement of the slider towards the first position may cause rotation of the first and second jaws towards a closed configuration in which the tool portions contact one another and movement of the slider towards the second position may cause rotation of the first and second jaws towards an open configuration in which the tool portions are spaced apart.

In such embodiments of the invention, antagonistically actuating the first and second portions of the actuation member may rotate the first and second jaws between a closed configuration and an open configuration.

In embodiments of the invention the tool portions may be configured as scissor blades, forceps, a dissector or a grasper. Further, in embodiments of the invention, the tool portions may be configured to form any suitable bipolar tool which may benefit from being driven by a single actuation member comprising antagonistically actuatable first and second portions. Accordingly, actuation mechanisms according to the invention may be adapted to provide a range of devices that are suitable for performing different tasks.

In embodiments of the invention the actuation mechanism may further comprise a housing comprising a first guide and a second guide; wherein, when the slider moves along the slider axis, the first protrusion is guided by the first guide and the second protrusion is guided by the second guide.

In such embodiments of the invention the guides may support the slider to stop it from rotating or twisting about the slider axis due to forces exerted on the protrusions by the jaws.

The guides may be adapted to support the protrusions by any suitable means. For example, in some embodiments of the invention, the first and second guides may be channels within which the protrusions are slidably receivable. In other embodiments of the invention, each guide may be a ridge and each protrusion may comprise a channel within which the respective guide is slidably receivable.

According to a second aspect of the invention there is provided a surgical instrument comprising a shaft, an articulated portion coupled to the shaft and an end effector coupled to the articulated portion, which end effector comprises an actuation mechanism according to the first aspect of the invention.

The surgical instrument may be used for surgical procedures and may be a robotic surgical instrument. The articulated portion may be actuated to facilitate movement of the end effector relative to the shaft with up to six degrees of freedom. Further, the articulated portion may be actuated by a plurality of tendons which extend along the shaft to actuators and motors, for example, which may drive actuation of the tendons.

In use the end effector, articulated portion and shaft may be positioned as required relative to the patient such that the end effector may be manipulated (via actuation of the articulated portion) and actuated via the actuation mechanism to perform tasks required for the relevant surgical procedure. More particularly, the end effector may be actuated by antagonistically actuating the first and second portions of the actuation member in order to move the slider along the slider axis which, in turn, causes rotation of the jaws.

BRIEF DESCRIPTION OF THE DRAWINGS

The invention will now be described by way of example only with reference to the accompanying drawings in which.

DETAILED DESCRIPTION OF THE EMBODIMENTS

Figure 1:
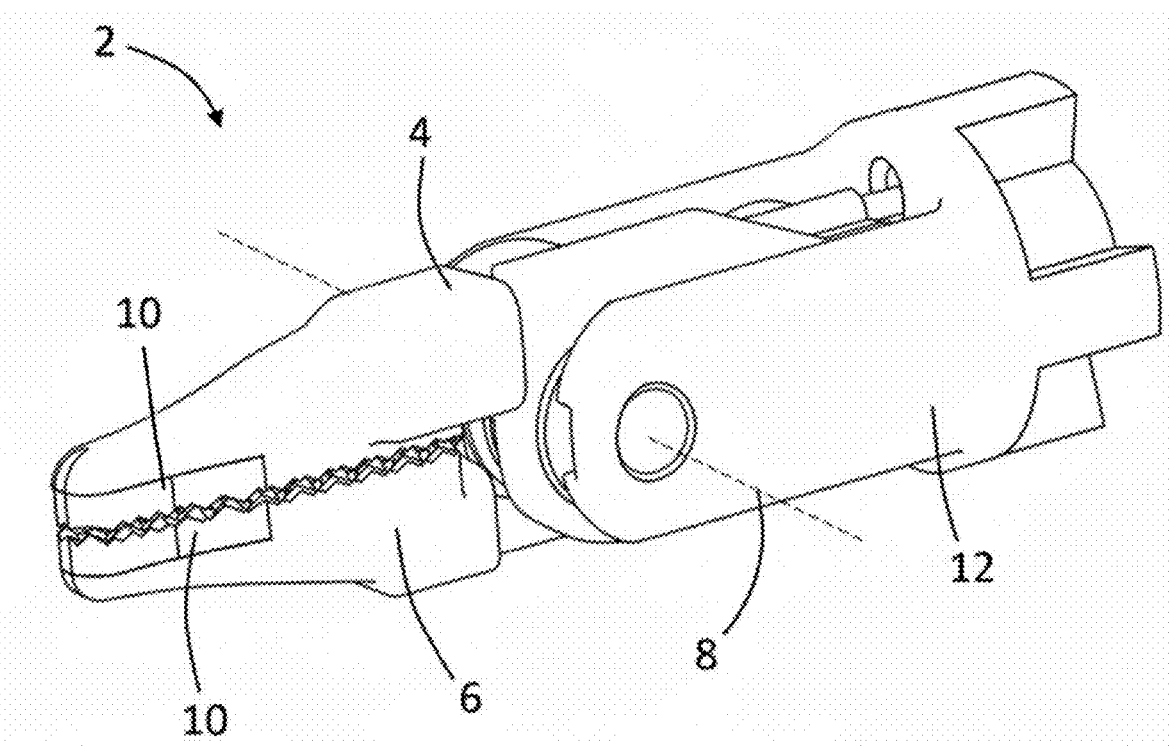
FIG. 1 is a schematic representation of an actuation mechanism according to an embodiment of the first aspect of the invention.
Figure 2:
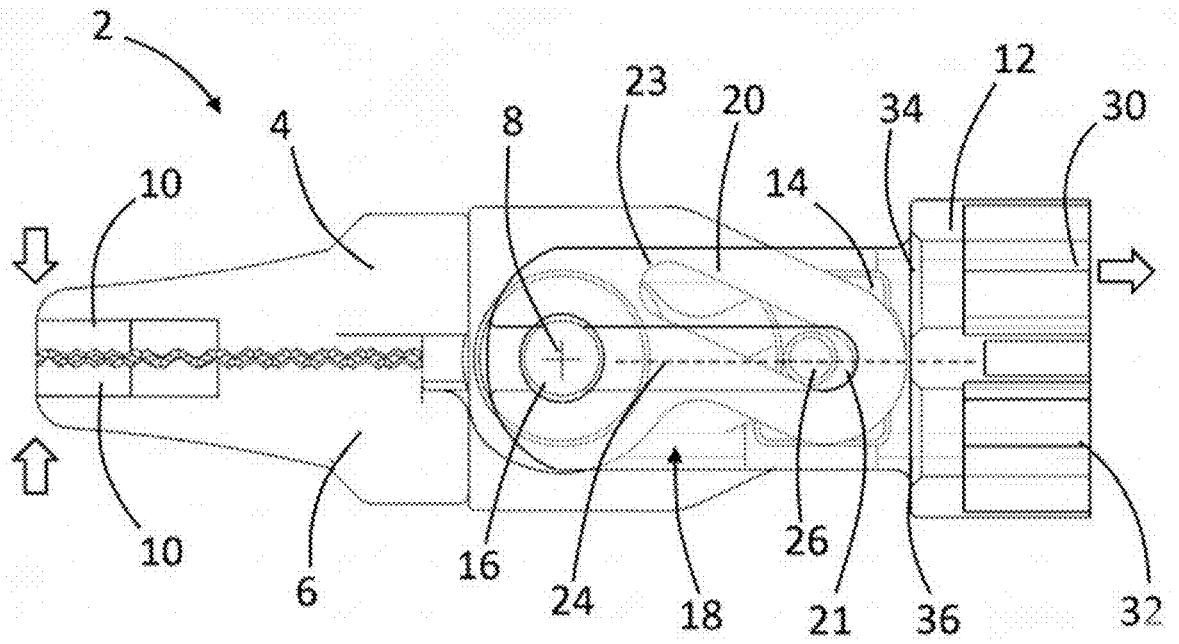
FIG. 2 is a schematic representation of the actuation mechanism shown in FIG. 1 with first and second jaws in a closed configuration.
Figure 3:
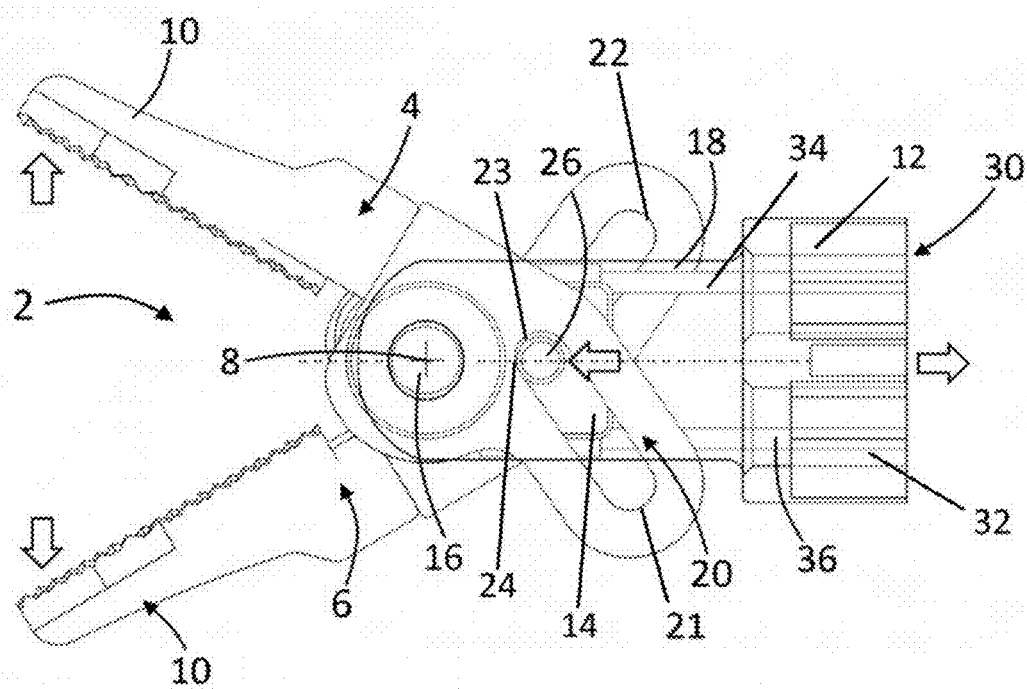
FIG. 3 is a schematic representation of the actuation mechanism shown in FIG. 1 with first and second jaws in an open configuration.

Referring initially to FIGS. 1 to 3, an actuation mechanism according to an embodiment of the invention is designated generally by the reference numeral 2. The actuation mechanism 2 comprises a first jaw 4 and a second jaw 6 each rotatable about a jaw axis 8. Each jaw 4, 6 comprises a tool portion 10. The jaws 4, 6 are rotatable between a closed configuration in which the tool portions 10 contact one another, as shown in Figures land 2, and an open position in which the tool portions 10 are spaced apart from one another as shown in FIG. 3.

In this embodiment of the invention the tool portions 10 form a grasper, although in other embodiments the jaws 4, 6 may comprise tool portions forming any suitable type of tool with two oppositely rotatable jaws such as scissors, forceps or a dissector.

The actuation mechanism 2 also comprises a housing 12 which is adapted to conceal and protect internal components of the actuation mechanism 2. This may reduce the risk of moving parts becoming blocked, obstructed or damaged. The housing 12 also has a substantially smooth, regular and continual outer surface with minimal sharp edges or corners. If the actuation mechanism 2 is in use as part of a surgical instrument, the housing 12 may protect internal tissues of a patient from irregular surfaces of parts of the actuation mechanism 2.

Referring now to FIGS. 2 to 6, and as shown particularly in FIGS. 2 and 3, the actuation member 2 further comprises a slider 14, a return 16 and an actuation member 18. Also, the first jaw 4 comprises a first slot 20 and the second jaw 6 comprises a second slot 22.

Figure 4:
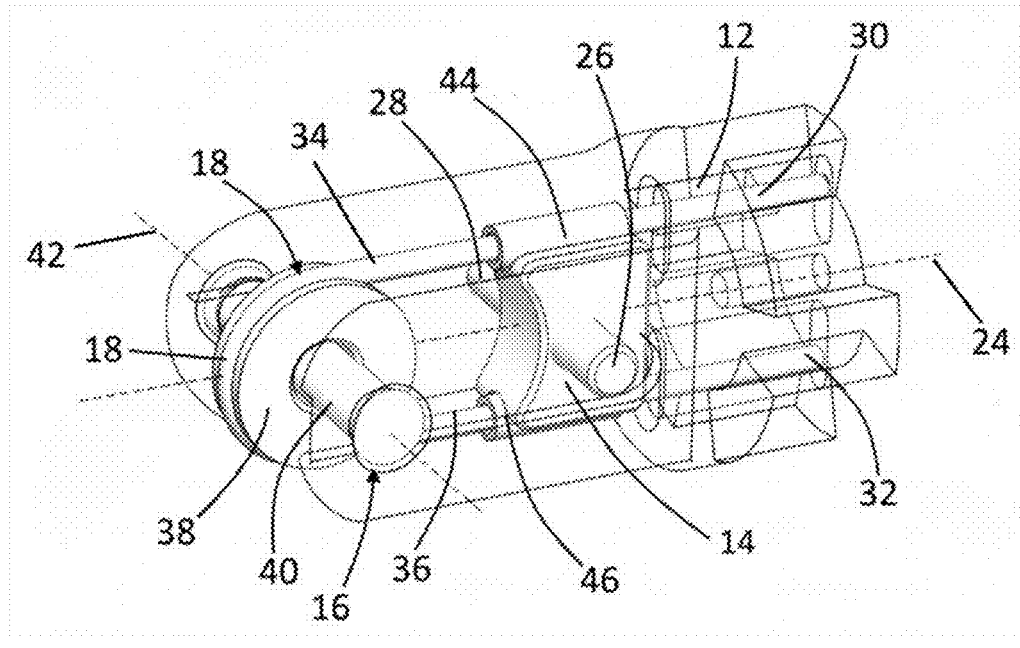
FIG. 4 is a schematic representation of a slider, actuation member, return and housing that each form part of the actuation mechanism shown in FIG. 1.
Figure 5:
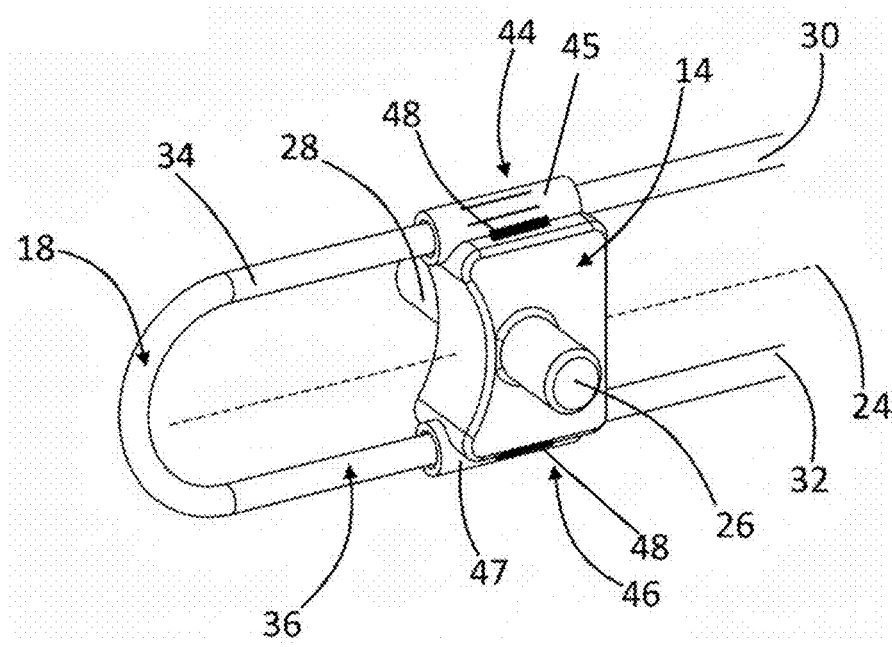
FIG. 5 is a schematic representation of the slider and actuation mechanism shown in FIG. 4.
Figure 6:
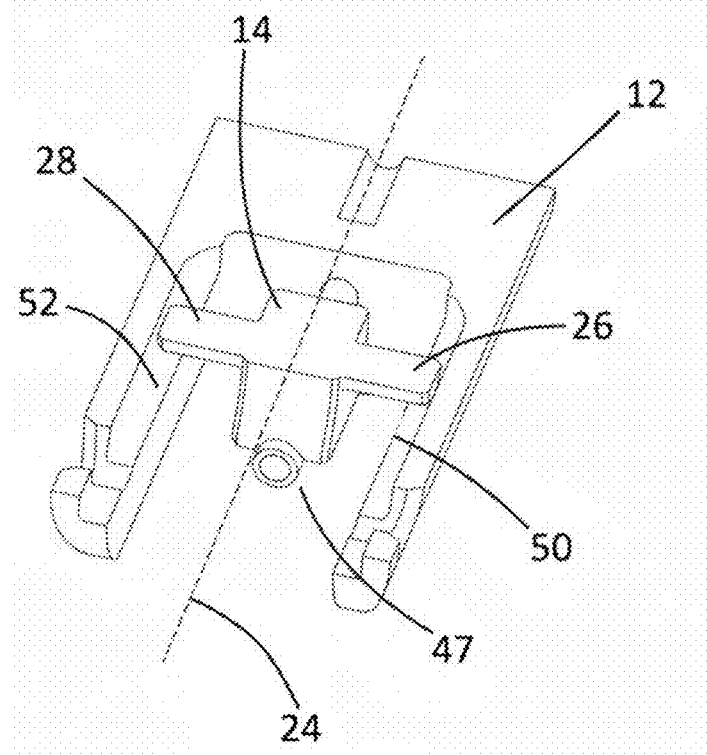
FIG. 6 is a cross-sectional view of the slider and housing shown in FIG. 4.

The slider 14 is movably engageable with the first and second jaws 4, 6 and, in particular, is moveable along a slider axis 24 between a first position, as shown in FIG. 2, and a second position, as shown in FIG. 3. The slider 14 comprises a first protrusion 26 slidably receivable within the first slot 20 and a second protrusion 28 as shown in FIGS. 4, 5 and 6 slidably receivable within the second slot 22. Each slot 20, 22 extends in a direction which is non-parallel to the slider axis 24 when the respective protrusion 26, 28 is engaged with the slot 20, 22. Further, each slot 20, 22 comprises a first end 21 positioned to receive the respective protrusion 26, 28 when the slider 14 is in the first position, as shown in FIG. 2, and a second end 23 positioned to receive the respective protrusion 26, 28 when the slider 14 is in the second position, as shown in FIG. 3. This means that movement of the slider 14 causes rotation of the first jaw 4 in a first sense and rotation of the second jaw 6 in a second sense opposite to the first. More specifically, movement of the slider 14 towards the first position causes rotation of the jaws 4, 6 towards the closed configuration and movement of the slider towards the second position causes rotation of the jaws 4, 6 towards the open configuration.

The angle of the slots 20, 22 relative to the slider axis 24, and the shape of the slots 20, 22 may be adapted to suit the application. In particular, each slot 20, 22 may be adapted so that the angle of each slot 20, 22 when the slider 14 is in a given position is suitable to allows an appropriate magnitude of force to be applied by the jaws 4, 6 when they are at a particular angle of rotation about the jaw axis 8. For example, the shallower the angle between each slot 20, 22 and the slider axis 24 when the slider is in the first position (shown in FIG. 2), the greater the force that the jaws 4, 6 may apply when they are at, or close to, the closed configuration. This is because a shallower angle results in less force being spent causing the jaws 4, 6 to rotate and overcoming friction between the first and second protrusions 26, 28 and the respective slots 20, 22. Increasing the force with which the jaws 4, 6 can close may be particularly useful in surgical applications, for example, in which the jaws 4, 6 may be used to grasp a small object such as a needle. Being able to hold the needle as firmly as possible may improve the safety and confidence with which the actuation mechanism may be used.

The return 16 is attachable to the actuation mechanism 2, more specifically to the housing 12 and is spaced apart from the slider 14. The actuation member 18 is operably engageable with both the slider 14 and the return 16 and comprises a first end 30, a second end 32, a first portion 34 and a second portion 36. The first portion 34 extends from the first end 30 to the return 16 while the second portion 36 extends from the return 16 to the second end 32. The first portion 34 is fixable to the slider 14. This means that, in use, movement of the first portion 34 away from the return 16 causes the slider 14 to move towards the first position, as shown in FIG. 2. Conversely, movement of the second portion 36 away from the return 16 causes the first portion 34 to move towards the return and therefore causes the slider 14 to move towards the second position, as shown in FIG. 3. As mentioned above, movement of the slider between the first and second positions causes the jaws 4, 6 to rotate between the closed and open configurations respectively. Hence, antagonistic actuation of the actuation member 18 causes articulation of the jaws 4, 6.

As shown particularly in FIG. 4, the return 16 comprises a pulley 38 and an axle 40. The axle 40 is supported by the housing 12 and extends along a return axis 42. The axle 40, in turn, supports the pulley 38 which is rotatable about the return axis 42. In this embodiment of the invention, the pulley 38 is freely rotatable about the axis 40 to reduce friction experienced when the actuation member 18 is actuated in either direction, i.e. moving either the first end 30 or the second end 32 away from the return 16. In other embodiments of the invention the pulley may be fixed to the axle and the axle may be rotatable relative to the housing, or the pulley and axle may both be fixed and the pulley may be adapted to facilitate the actuation member sliding over the pulley with a low coefficient of friction, for example.

In this embodiment of the invention, the return axis 42 is coaxial with the jaw axis 8 as shown in FIGS. 1 to 3. Further, the first and second jaws 4, 6 are rotatably engageable with the axle 40 such that the jaws 4, 6 are supported by, and rotatable about, the axle 40. Positioning the return 16 such that the return axis 42 is coaxial with the jaw axis 8 reduces the longitudinal space required by the jaws 4, 6, return 16 and slider 14 and allows for the actuation mechanism 2 to be more compact overall. It also reduces the complexity of the actuation mechanism 2 in terms of the number of parts required which may reduce manufacturing costs and improve the durability of the actuation mechanism 2 as there are fewer parts which may fail.

The slider 14 comprises a first member receiving portion 44 and a second member portion 46. The actuation member 18 is fixable to the slider 14 between the first end 30 and the return 16 via the first member receiving portion 44. Further, the actuation member 18 is slidably engageable with the slider 14 between the return 16 and the second end 32 and, more particularly, is slidably receivable within the second member receiving portion 46. Although slidably engaging the second portion 36 of the actuation member 18 with the slider does not directly affect the movement of the slider 14 along the slider axis 24, it may improve the stability of the slider 14 as it moves along the slider axis 24. In particular, it may reduce the likelihood of the slider 14 twisting due to forces exerted on the first and second protrusions 26, 28 by the respective jaws 4, 6.

In this embodiment of the invention, the first and second member receiving portions 44, 46 are first and second ferrules 45, 47 which are each attached to the slider via a joint 48, as shown in FIG. 5. Each joint 48 may be created by laser spot welding or any other suitable means for affixing the ferrules to the slider. In order to fix the first portion 34 of the actuation member 18 to the slider 14, the first ferrule 45 is crimped to the actuation member 18. Meanwhile, the second ferrule 47 remains uncrimped so that the actuation member 18 may slide freely through it.

Referring now to FIG. 6, the housing 12 comprises a first guide 50 and a second guide 52. In use, when the slider 14 moves along the slider axis 24, the first protrusion 26 is guided by the first guide 50 and the second protrusion 28 is guided by the second guide 52. In particular, the guides may support the slider 14 to stop it from rotating or twisting about the slider axis 24 due to forces exerted on the protrusions 26, 28 by the jaws 4, 6.

In this embodiment of the invention, the first and second guides 50, 52 are channels within which the protrusions 26, 28 are slidably receivable. However, in other embodiments of the invention, the guides may be adapted to support the protrusions by any suitable means. For example, each guides may be a ridge and each protrusion may comprise a channel within which the respective guide is slidably receivable.

Preferences and options for a given aspect, feature or parameter of the invention should, unless the context indicates otherwise, be regarded as having been disclosed in combination with any and all preferences and options for all other aspects, features and parameters of the invention.

The invention claimed is:

1. An actuation mechanism comprising:
   a first jaw rotatable about a jaw axis and comprising a first slot;
   a second jaw rotatable about the jaw axis and comprising a second slot;
   a slider moveable along a slider axis between a first position and a second position and movably engageable with the first and second jaws, which slider comprises a first protrusion slidably receivable within the first slot and a second protrusion slidably receivable within the second slot, wherein each slot extends in a direction which is non-parallel to the slider axis when the respective protrusion is engaged with the slot;
   a return attachable to the actuation mechanism and spaced apart from the slider; and
   an actuation member operably engageable with both the slider and the return, the actuation member comprising a first end, a second end, a first portion that extends from the first end to the return, and a second portion that extends from the return to the second end, the first portion being fixable to the slider whereby movement of the first portion away from the return causes the slider to move towards the first position and movement of the second portion away from the return causes the slider to move towards the second position, wherein the actuation member is slidably engageable with the slider between the return and the second end, wherein the slider comprises a first member receiving portion and a second member portion, and the actuation member is fixable to the slider via the first member receiving portion and slidably receivable within the second member receiving portion.

2. An actuation mechanism according to claim 1 wherein the return comprises a pulley rotatable about a return axis and the actuation member passes around the pulley between the first portion and the second portion.

3. An actuation mechanism according to claim 2 wherein the return further comprises an axle that extends along the return axis and supports the pulley.

4. An actuation mechanism according to claim 3 wherein the return axis is coaxial with the jaw axis.

5. An actuation mechanism according to claim 4 wherein the first and second jaws are rotatably engageable with the axle such that the first and second jaws are supported by, and rotatable about, the axle.

6. An actuation mechanism according to claim 1 wherein each jaw comprises a tool portion, movement of the slider towards the first position causes rotation of the first and second jaws towards a closed configuration in which the tool portions contact one another and movement of the slider towards the second position causes rotation of the first and second jaws towards an open configuration in which the tool portions are spaced apart.

7. An actuation mechanism according claim 6 wherein the tool portions are configured as scissor blades, forceps, a dissector or a grasper.

8. An actuation mechanism according to claim 1 further comprising a housing comprising a first guide and a second guide; wherein, when the slider moves along the slider axis, the first protrusion is guided by the first guide and the second protrusion is guided by the second guide.

9. A surgical instrument comprising a shaft, an articulated portion coupled to the shaft and an end effector coupled to the articulated portion, which end effector comprises an actuation mechanism according to claim 1.

\* \* \* \* \*